US00PP08242P

United States Patent [19]

Meilland

[11] Patent Number: Plant 8,242

[45] Date of Patent: Jun. 1, 1993

[54] MINIATURE ROSE PLANT—MEINOCHOT VARIETY

[75] Inventor: Alain A. Meilland, Antibes, France

[73] Assignee: The Conard-Pyle Company, West Grove, Pa.

[21] Appl. No.: 798,108

[22] Filed: Nov. 26, 1991

[51] Int. Cl.[5] ..... A01H 5/00
[52] U.S. Cl. ..... Plt./10
[58] Field of Search ..... Plt. 10

*Primary Examiner*—Howard J. Locker

*Attorney, Agent, or Firm*—Burns, Doane, Swecker & Mathis

[57] ABSTRACT

A new and distinct variety of rose plant of the miniature class is provided which abundantly forms attractive long-lasting very double currant red blossoms of stable coloration. The plant is bushy, compact and low growing, and forms very vigorous vegetation. The plant is well adapted to greenhouse forcing while grown in small containers, and is particularly well suited for use as a flowering pot plant when grown indoors or outdoors. Additionally, the plant is not particularly affected by cryptogamic diseases.

1 Drawing Sheet

SUMMARY OF THE INVENTION

The new variety of miniature rose plant was created by artificial pollination wherein two parents were crossed which previously had been studied in the hope that they would contribute the desired characteristics. The female parent (i.e., the seed parent) was the product of the pollination of the Meidanu variety (also known as Tamango, U.S. Plant Pat. No. 2,857) by the Alain variety (nonpatented in the United States). The male parent (i.e., the pollen parent) of the new variety was the Ruimired variety (U.S. Plant Pat. No. 5,770). The parentage of the new variety can be summarized as follows:

(Meidanu × Alain) × Ruimired.

The seeds resulting from the above pollination were sown and 105 plantlets were obtained which were physically and biologically different from each other. Selective study resulted in the identification of a single plant of the new variety.

It was found that the new variety of miniature rose plant of the present invention possesses the following combination of characteristics:

(a) forms in abundance attractive very double long-lasting blossoms which are currant red and of a stable coloration which resists bluing,
(b) forms very vigorous vegetation,
(c) exhibits a bushy, compact, and low growth habit,
(d) is well adapted to greenhouse forcing while growing in small containers,
(e) is not particularly affected by cryptogamic diseases.

The new variety well meets the needs of the horticultural industry. It is particularly well-suited for use as attractive ornamentation as a flowering pot plant when grown indoors or outdoors. For instance, the new variety grows well in four inch pots.

The new variety has been found to undergo asexual propagation in France by a number of routes, including budding, grafting, cuttage, etc. Asexual propagation by the above mentioned methods as performed in France has shown that the characteristics of the new variety are strictly transmissible from one generation to another.

The new variety has been named the Meinochot variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were one year of age and were observed during June while growing on their own roots outdoors at LeCannet des Maures, Var, France.

FIG. 1 — illustrates a specimen of a young shoot;

FIG. 2 — illustrates specimens of two floral buds before the opening of the sepals;

FIG. 3 — illustrates specimens of two floral buds at the opening of the sepals;

FIG. 4 — illustrates specimens of two floral buds at the opening of the petals;

FIG. 5 — illustrates specimens of two flowers during the course of opening;

FIG. 6 — illustrates a specimen of a flower in the course of opening — plan view — obverse;

FIG. 7 — illustrates a specimen of a flower in the course of opening — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of mature wood;

FIG. 14 — illustrates specimens of leaves with three leaflets with the upper surface being shown at the top and the under surface being shown at the bottom;

FIG. 15 — illustrates specimens of leaves with five leaflets with the upper surface being shown at the left and the under surface being shown at the right; and FIG. 16 — illustrates specimens of leaves with seven leaflets with the under surface being shown at the left and the upper surface being shown at the right.

DETAILED DESCRIPTION

Figures 1, 2, 3, 4, 5, 6, 7, 8, 9, 10, 11, 12, 13, 14, 15, 16:
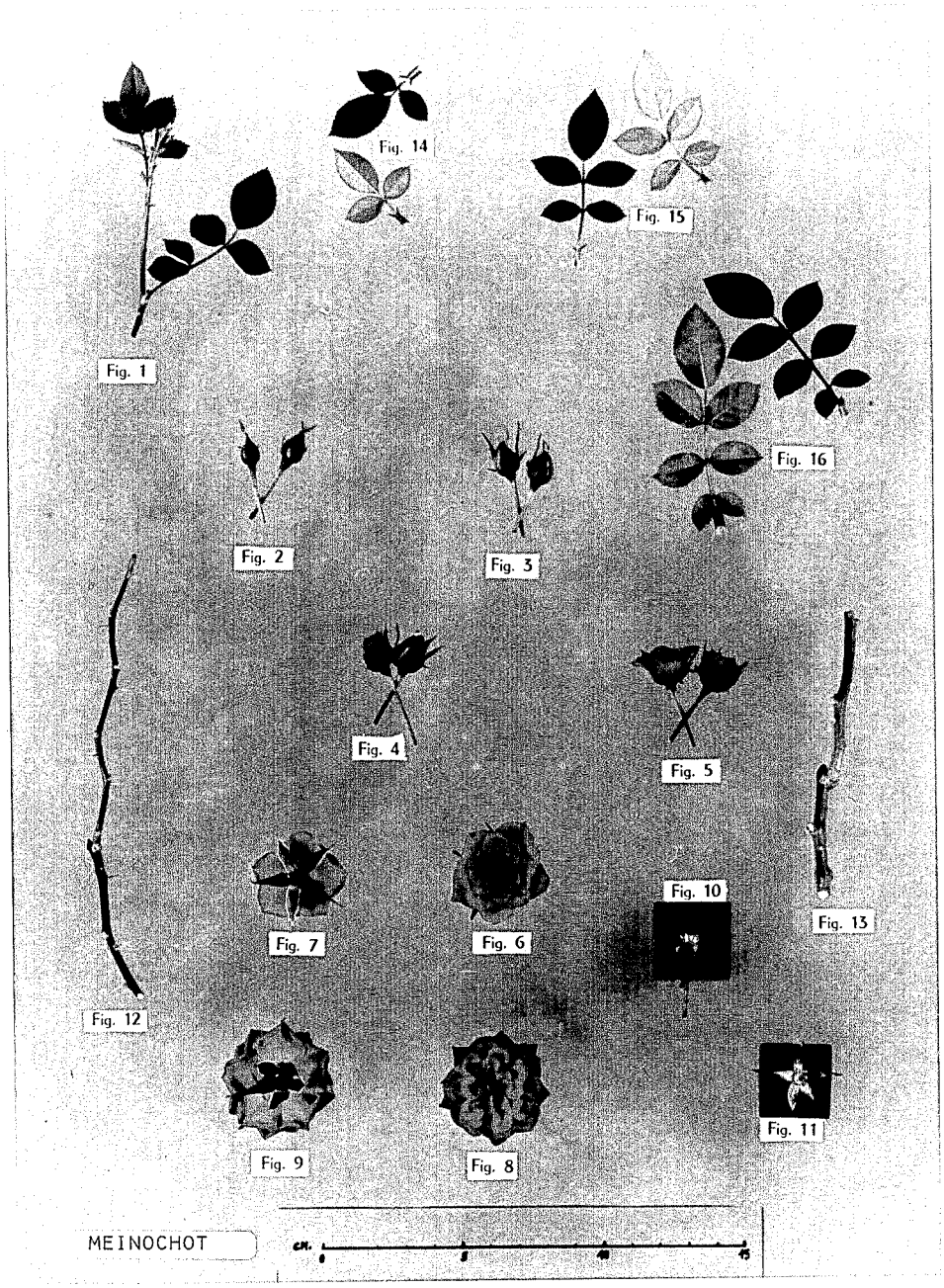

The chart used in the identification of the colors is that of The Royal Horticultural Society (R.H.S. Colour Chart). The terminology which precedes reference to the chart has been added to indicate the corresponding colors in common terms. The description is based on one year old specimens of the new variety which were observed during June while growing on their own roots outdoors at LeCannet des Maures, Var, France.

Class: Miniature.

Plant:

*Height.*—approximately 25 to 30 cm. On average when grown outdoors on own roots, and approximately 15 to 20 cm. On average above the pot when grown in 4 inch pots.

*habit.*—Compact and bushy.

Branches:

*Color.*—Young stems: light green, Green Group 143C.

Adult wood: medium green, Green Group 143A.

*Thorns.*—Size: small. Quantity: average. Color: pinkish on young stems and pinkish green on mature wood.

Leaves:

Petioles.—Upper surface: striped, reddish brown on young foliage and medium green on adult foliage with more or less glandular edges. Under surface: medium green with a few prickles.

Stipules.—Adnate, pectinate, not wide and linear.

*Leaflets.*—Number: 3, 5, and 7 (most often). Shape: elliptic. Serration: single and regular. Texture: consistent. General appearance: dense, abundant, and semi-matte. Color (young foliage): Upper surface: medium green, Green Group 143A. Under surface: light green, Green Group 143C. Color (adult foliage): Upper surface: dark green, Green Group 137A. Under surface: greyish green, Greyed-Green Group 191A.

Inflorescence:

*Number of flowers.*—Approximately 1 to 6 per stem.

*Peduncle.*—Light green, covered with glandular aciculae, its length is approximately 3 to 4.5 cm. on average.

*Sepals.*—Upper surface: tomentose and greenish in coloration. Under surface: medium green, and the outer sepals are only slightly appendiculated.

*Buds.*—Shape: globular. Length: approximately 1.5 cm. on average. Size: small. Color upon opening: Upper surface: currant red, Red Group 46A. Under surface: Currant red, Red Group 46A.

*Flower.*—Form: as a flat cup at opening, then like an umbrella when fully open, and very double.

Diameter: approximately 3.5 cm. on average. Color (when opening begins): Upper surface: currant red, Red Group 46A. Under surface: currant red, Red Group 46A. Color (when blooming): Upper Surface: currant red, Red Group 46B. Under surface: currant red, Red group 46B. Color (at end of blooming): Upper surface: currant red, Red Group 46B. Under surface: currant red, Red Group 46B. Sometimes the stamens and pistils are fully visible at the center of the open bloom, thereby revealing straw-yellow coloration at the center of the bloom. Fragrance: none. Lasting quality: very long. Petal number: approximately 61 to 78 on average. Petal shape: oval. Petal texture: consistent. Petal drop: good. Anthers: bright yellow in coloration. Stamen number: approximately 16 on average. Filaments: very short and light fuschia in coloration. Pistil number: approximately 16 on average. Stigmas: straw-like in coloration. Styles: dark fuschia in coloration, only slightly twisted, and of irregular heights. Receptacle: light green, smooth and in longitudinal section is narrow and in the shape of a pitcher at the dehiscence of the anthers.

Development:

*Vegetation.*—Very vigorous.

*blooming.*—Very abundant.

*Aptitude to bear fruit.*—None.

*resistance to diseases.*—Good.

*Resistance to frost.*—Good.

I claim:

1. A new and distinct variety of miniature rose plant characterized by the following combination of characteristics:

(a) forms in abundance attractive very double long-lasting blossoms which are currant red and of a stable coloration which resists bluing, (b) forms very vigorous vegetation, (c) exhibits a bushy, compact, and low growth habit, (d) is well adapted to greenhouse forcing while growing in small containers, and (e) is not particularly affected by cryptogamic diseases;

substantially as herein shown and described.

* * * * *

MEINOCHOT
CM.
0
5
10
15